United States Patent
Amann

(10) Patent No.: US 9,352,163 B2
(45) Date of Patent: *May 31, 2016

(54) ELECTROCARDIOGRAM IDENTIFICATION

(71) Applicant: ZOLL Medical Corporation, Chelmsford, MA (US)

(72) Inventor: John Amann, Worcester, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/831,128

(22) Filed: Aug. 20, 2015

(65) Prior Publication Data

US 2015/0352368 A1    Dec. 10, 2015

Related U.S. Application Data

(63) Continuation of application No. 14/039,727, filed on Sep. 27, 2013, now Pat. No. 9,144,390.

(51) Int. Cl.
| | |
|---|---|
| *A61B 5/04* | (2006.01) |
| *A61N 1/39* | (2006.01) |
| *A61B 5/0432* | (2006.01) |
| *A61B 5/00* | (2006.01) |
| *A61B 5/046* | (2006.01) |
| *A61B 5/0464* | (2006.01) |
| *A61B 5/0404* | (2006.01) |
| *A61B 5/0408* | (2006.01) |

(52) U.S. Cl.
CPC .............. *A61N 1/3925* (2013.01); *A61B 5/046* (2013.01); *A61B 5/0464* (2013.01); *A61B 5/04325* (2013.01); *A61B 5/742* (2013.01); *A61N 1/3931* (2013.01); *A61N 1/3937* (2013.01); *A61N 1/3968* (2013.01); *A61N 1/3993* (2013.01); *A61B 5/0006* (2013.01); *A61B 5/0404* (2013.01); *A61B 5/04085* (2013.01); *A61B 2505/01* (2013.01)

(58) Field of Classification Search
USPC .................................................. 607/509–510
See application file for complete search history.

(56) References Cited

U.S. PATENT DOCUMENTS

| | | |
|---|---|---|
| 2006/0219776 A1 | 10/2006 | Finn |
| 2010/0234910 A1 | 9/2010 | Parascandola et al. |
| 2010/0297594 A1 | 11/2010 | Sullivan et al. |
| 2011/0060378 A1 | 3/2011 | Tuysserkani |
| 2011/0172550 A1 | 7/2011 | Martin et al. |
| 2011/0202100 A1 | 8/2011 | Tan et al. |
| 2012/0071942 A1* | 3/2012 | Kamath ......... A61B 17/320068 607/14 |
| 2012/0123224 A1 | 5/2012 | Packer et al. |

OTHER PUBLICATIONS

International Search Report & Written Opinion, PCT/US2014/057833, mailed Mar. 3, 2015, 14 pages.

* cited by examiner

*Primary Examiner* — Nicole F Lavert
(74) *Attorney, Agent, or Firm* — Fish & Richardson P.C.

(57) ABSTRACT

A defibrillating system includes a processor coupled to a memory. The processor and the memory are configured to identify a treatment event associated with treatment of a victim with the defibrillating system, and transmit a representation of a portion of an ECG signal associated with the identified treatment event. In some cases, the processor and the memory are configured to identify the portion of the ECG signal associated with the identified treatment event. In some cases, the portion of the ECG signal is of a predetermined length of time having a start time and an end time based on a time associated with the identified treatment event.

23 Claims, 10 Drawing Sheets

ELECTROCARDIOGRAM IDENTIFICATION

CROSS-REFERENCE TO RELATED APPLICATIONS

This is a continuation of and claims priority under 35 U.S.C. §120 to U.S. patent application Ser. No. 14/039,727, filed Sep. 27, 2013. All subject matter set forth in the above referenced application is hereby incorporated by reference into the present application as if fully set forth herein.

TECHNICAL FIELD

This invention relates to identification of portions of an electrocardiogram (ECG) trace, for instance, identification of portions of ECG traces of a victim treated by a defibrillating system such as an automated external defibrillator (AED).

BACKGROUND

Sudden health problems such as sudden cardiac arrest and injuries caused by accidents kill thousands of people and cause permanent injury every year. Fast and competent care to resuscitate such victims of these problems can be essential to positive outcomes in such situations. For example, it is said that the chance of surviving a sudden cardiac arrest falls by ten percent for every minute of delay in providing effective treatment.

Resuscitation treatments for patients suffering from cardiac arrest generally include clearing and opening the patient's airway, providing rescue breathing for the patient, and applying chest compressions to provide blood flow to the victim's heart, brain, and other vital organs. If the patient has a shockable heart rhythm (ventricular fibrillation or pulseless ventricular tachycardia), resuscitation also may include defibrillation therapy. Along with such action, an electrocardiogram (ECG) signal for the patient may be electronically captured, displayed, and monitored, so that rescuers can determine when the patient's heart has returned to normal or near-normal operation, and determine when the heart exhibits a shockable rhythm.

SUMMARY

In a general aspect, a defibrillating system includes a processor coupled to a memory. The processor and the memory are configured to identify a treatment event associated with treatment of a victim with the defibrillating system, and transmit a representation of a portion of an ECG signal associated with the identified treatment event.

Embodiments may include one or more of the following features.

The portion of the ECG signal is of a predetermined length of time having a start time and an end time based on a time associated with the identified treatment event. In some cases, the predetermined length of time is less than about 15 seconds.

The processor and the memory are configured to identify the portion of the ECG signal associated with the identified treatment event. In some cases, identifying the portion of the ECG signal comprises selecting a portion of the ECG signal having a predetermined length of time.

The processor and the memory are configured to identify multiple treatment events associated with treatment of the victim with the defibrillating system. In some cases, the processor and the memory are configured to transmit an identifier of each of the multiple treatment events. In some cases, the processor and the memory are configured to receive a selection of a particular one of the multiple treatment events. In some cases, the processor and the memory are configured to transmit the portion of the ECG signal associated with the particular one of the multiple treatment events.

Transmitting the portion of the ECG signal includes displaying the portion of the ECG signal on a display interface of the defibrillating system.

Transmitting the portion of the ECG signal includes transmitting the portion of the ECG signal to a computing device.

The processor and the memory are configured to detect that the defibrillating system has been disconnected from the victim. In some cases, the processor and the memory are configured to detect that the defibrillating system has been disconnected by detecting a loss of impedance in a circuit that includes the defibrillating system and the victim.

The portion of the ECG signal corresponds to a time period in which the defibrillating system performed an analysis of the victim's rhythm.

The portion of the ECG signal corresponds to a time period during which the defibrillating system was first connected to the victim.

In a general aspect, a defibrillating system includes a processor coupled to a memory. The processor and the memory are configured to, during treatment of a victim with an automated external defibrillator (AED), associate each of multiple portions of an electrocardiogram (ECG) signal with a corresponding treatment event. The processor and the memory are configured to detect that the AED has been disconnected from the victim; responsive to the disconnection of the AED, display identifiers of at least some of the treatment events; receive a user selection of one of the displayed treatment events; and display a representation of the portion of the ECG signal associated with the selected treatment event.

In a general aspect, a method includes identifying, by a processor of a defibrillating system, a treatment event associated with treatment of a victim with the defibrillating system; and transmitting, by the processor, a representation of a portion of an ECG signal associated with the identified treatment event.

Embodiments may include one or more of the following features.

The portion of the ECG signal is of a predetermined length of time having a start time and an end time based on a time associated with the identified treatment event. In some cases, the predetermined length of time is less than about 15 seconds.

The defibrillating system includes an AED.

The method includes identifying the portion of the ECG signal associated with the identified treatment event. In some cases, identifying the portion of the ECG signal includes selecting a portion of the ECG signal having a predetermined length of time.

Identifying a treatment event includes identifying multiple treatment events associated with treatment of the victim with the defibrillating system. In some cases, the method includes transmitting an identifier of each of the multiple treatment events. In some cases, the method includes receiving a selection of a particular one of the multiple treatment events. In some cases, the method includes transmitting the portion of the ECG signal comprises transmitting the portion of the ECG signal associated with the particular one of the multiple treatment events.

Transmitting the portion of the ECG signal comprises displaying the portion of the ECG signal on a display interface of the defibrillating system.

Transmitting the portion of the ECG signal comprises transmitting the portion of the ECG signal to a computing device.

The method includes detecting that the defibrillating system has been disconnected from the victim. In some cases, detecting that the defibrillating system has been disconnected includes detecting a loss of impedance in a circuit that includes the defibrillating system and the victim. In some cases, the method includes receiving confirmation from the user that the defibrillating system has been disconnected.

In a general aspect, a computer readable medium stores instructions for causing a computing system to identify a treatment event associated with treatment of a victim with the defibrillating system, and transmit a representation of portion of an ECG signal associated with the identified treatment event.

Embodiments may include one or more of the following features.

The portion of the ECG signal is of a predetermined length of time having a start time and an end time based on a time associated with the identified treatment event. In some cases, the predetermined length of time is less than about 15 seconds.

The instructions cause the computing system to identify the portion of the ECG signal associated with the identified treatment event. In some cases, identifying the portion of the ECG signal includes selecting a portion of the ECG signal having a predetermined length of time.

The instructions cause the computing system to identify multiple treatment events associated with treatment of the victim with the defibrillating system. In some cases, the instructions cause the computing system to receive a selection of a particular one of the multiple treatment events. In some cases, the instructions cause the computing system to transmit the portion of the ECG signal associated with the particular one of the multiple treatment events.

The techniques described herein can have one or more of the following advantages. Monitoring and storing portions of a victim's ECG trace on a defibrillating system, such as an automated external defibrillator (AED), allows a caregiver to view information about the victim's cardiac rhythm at a later point in time, which can aid in diagnosing and treating the victim. For instance, re-displaying a portion of the victim's ECG trace from a point in time when treatment was started and/or a portion of the victim's ECG trace prior to receiving a shock can provide information that can be used to diagnose the victim's condition. Knowledge of the victim's likely diagnosis can inform treatment of the victim, both at the rescue scene and in a hospital setting. The ability to view these traces at the rescue scene can enable skilled caregivers to make informed treatment decisions even if those caregivers were not present when the traces were recorded.

The details of one or more embodiments are set forth in the accompanying drawings and the description below. Other features and advantages will be apparent from the description, drawings, and claims.

DETAILED DESCRIPTION

An approach to collecting, storing, and transmitting one or more portions of a victim's ECG trace is described herein. The portions of the victim's ECG trace can be transmitted at a time subsequent to collecting and storing the ECG trace, such as upon request by a user of an AED during treatment of the victim or upon disconnecting the AED from the victim. For instance, the portions of the victim's ECG trace can be transmitted to a display interface of the AED for display, transmitted to a computing device for storage or display, or otherwise transmitted. It can be beneficial for a rescuer or medical professional to have access to information about earlier portions of the victim's ECG to aid in diagnosis and/or treatment of the victim. For instance, the portions of the victim's ECG trace can be associated with treatment events, such as determinations by the AED of whether the victim's cardiac rhythm was shockable or non-shockable. In one example, the portion of the victim's ECG trace when treatment was started and/or the portions of the victim's ECG trace prior to receiving a shock (or prior to a determination that the victim's rhythm was non-shockable) can be displayed on the AED, providing information that can be used by a caregiver to diagnose the victim's condition and/or to inform treatment decisions.

The ability to view portions of the victim's ECG trace at the rescue scene can provide critical, lifesaving information to a victim's caregivers. For instance, an initial caregiver may be a relatively untrained caregiver, such as a police officer, who does not know how to read ECG traces. As such, the initial caregiver may be unable to communicate information about the victim's initial ECG trace and information about portions of the ECG trace in the analysis periods to a highly trained caregiver that may arrive on the scene later. By providing the trained caregiver with the ability to view portions of the victim's ECG trace, the trained caregiver can have rapid access to information that can enable him to make more informed decisions about treatment options for the victim (e.g., information about the victim's condition when he first collapsed or information about the rhythms that triggered shock events). For instance, the caregiver can use this information to decide which medications to administer, whether to continue with CPR or defibrillation treatment, how urgently to bring the victim to an emergency room, and other decisions. In addition, the caregiver can communicate this information to other medical personnel, such as emergency room nurses or physicians, without having to download the ECG traces or transport the AED itself to the emergency room.

Figure 1A:
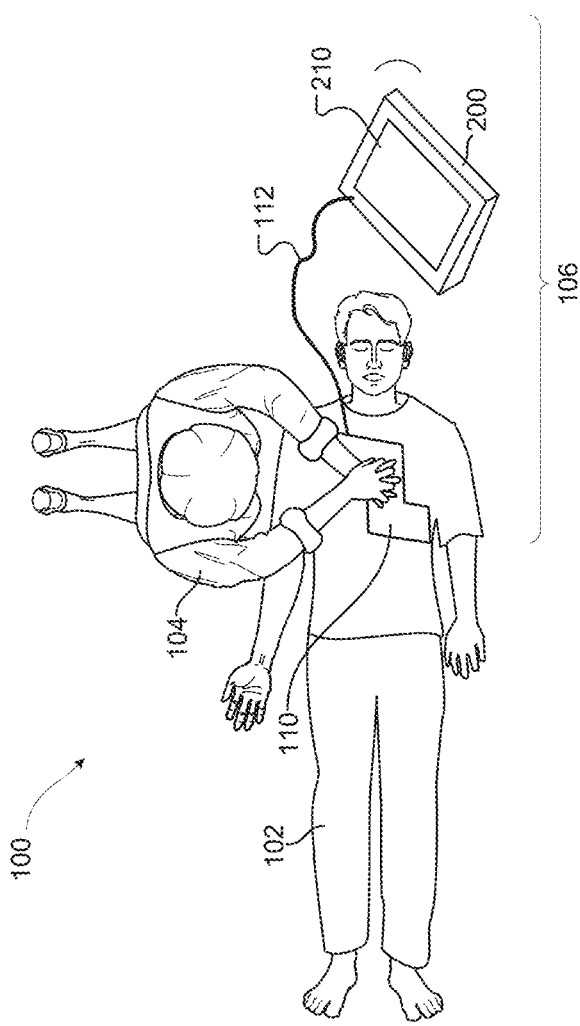
FIGS. 1A and 1B are diagrams of a rescue scene.

Referring to FIG. 1A, at a rescue scene 100, a caregiver 104 performs cardiopulmonary resuscitation (CPR) on a victim 102. The victim 102 may be, for instance, an individual who has apparently undergone sudden cardiac arrest. The caregiver 104 may be, for instance, a civilian responder with limited or no training in lifesaving techniques; a first responder, such as a police officer, firefighter, emergency medical technician (EMT), or paramedic; or a medical professional, such as a physician or nurse. The caregiver 104 may be acting alone or may be acting with assistance from one or more other caregivers, such as a partner police officer.

An electronic defibrillating system 106 includes a defibrillator, such as an automated external defibrillator (AED) 200, a professional defibrillator, or another type of defibrillating apparatus. The AED 200 is connected to electrode pads 110 placed on the victim's chest via one or more cables 112. The AED 200 provides defibrillation to the victim 102 as needed via the electrode pads 110 and instructs the caregiver 104 in performing CPR. The AED 200 stores information associated with the victim's cardiac rhythm (e.g., the victim's electrocardiogram (ECG) trace) and can later transmit one or more portions of the ECG trace to a display interface 210 of the AED 200 or to another computing device. For instance, representations of one or more portions of the ECG trace can be transmitted during treatment of the victim 102 or when the AED 200 is disconnected from the victim 102.

Figure 2:
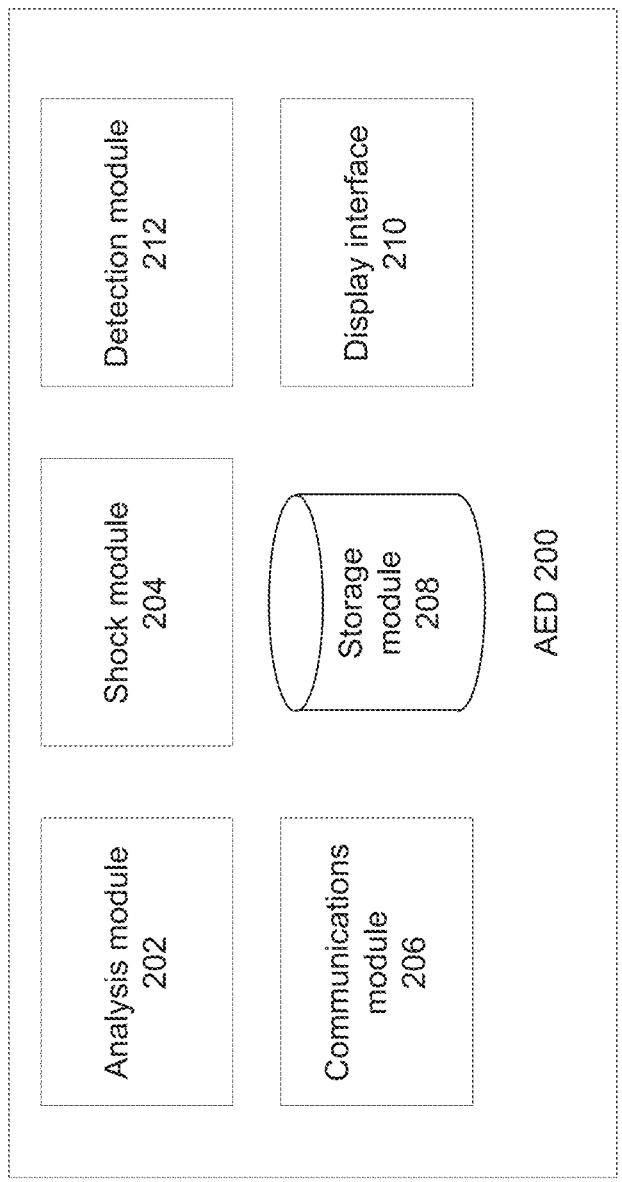
FIG. 2 is a block diagram of an AED.

Referring to FIG. 2, the AED 200 includes an analysis module 202 that determines whether the cardiac rhythm of the victim 102 is shockable. In one example, the analysis module 202 periodically (e.g., every minute, every 2 minutes, every 3 minutes, or another time period) monitors and analyzes the victim's rhythm for a short analysis period (e.g., 9 seconds, 12 seconds, 15 seconds, or another analysis period). The analysis module 202 identifies the victim's rhythm during the analysis period and determines whether the rhythm is shockable, for instance, based on characteristics of the waveform(s) in the rhythm. Example shockable rhythms (i.e., rhythms that can be treated by delivering a shock to the victim 102) include ventricular fibrillation, ventricular tachycardia, ventricular flutter, and other types of shockable rhythms. Example non-shockable rhythms (i.e., rhythms that cannot be treated effectively by delivering a shock to the victim 102) include asystole, bradycardia, pulseless electrical activity (PEA), idioventricular rhythms, normal rhythm, and other types of non-shockable rhythms.

If the victim's rhythm is shockable, a shock module 204 of the AED 200 causes a shock to be delivered to the victim 102 through the electrode pads 110. In some cases, the shock can be delivered automatically. In some cases, a communications module 206 of the AED 200 can prompt the caregiver 104 for a command to deliver a shock to the victim 102 or can present a "Clear" warning to the caregiver 104. If the victim's rhythm is non-shockable, the communications module 206 can instruct the caregiver to deliver chest compressions to the victim 102.

A treatment event is a determination (e.g., by the analysis module 202) of whether the victim's cardiac rhythm is shockable, e.g., following each analysis period or following an initial analysis period upon beginning treatment of the victim 102 with the AED 200. The portion of the ECG trace associated with each treatment event can correspond to the analysis period preceding the treatment event. The portion of the ECG trace associated with a particular treatment event can be of a predetermined length of time (e.g., the length of the analysis period, such as 9 seconds, 12 seconds, 15 seconds, or another length of time) and can have a start time and an end time based on a time associated with the particular treatment event. For instance, the end time of the portion of the ECG trace associated with a particular treatment event can be the time at which the treatment event occurred (e.g., the time at which the victim's rhythm was determined to be shockable or non-shockable), and the start time of the portion of the ECG trace can be earlier by the length of the analysis period (e.g., 9 seconds, 12 seconds, 15 seconds, or another amount of time earlier).

The analysis module 202 can identify the portion of the victim's ECG trace associated with one or more treatment events that occurred during treatment of the victim 102 with the AED 200. For instance, based on information indicative of the time at which a particular treatment event occurred and the length of time of the analysis period, the analysis module 202 can select the portion of the ECG trace that is associated with that particular treatment event.

A storage module 208 in the AED 200 stores the victim's ECG trace. The storage module 208 can be, e.g., a database, a file, or another type of data structure. In some examples, one or more portions of the ECG trace are stored, such as portions identified by the analysis module 202 as associated with treatment events. In some examples, the entire ECG trace is stored and each portion identified by the analysis module 202 as associated with a treatment event is marked, e.g., with a tag identifying the respective treatment event (e.g., a timestamp or a characteristic of the treatment event, such as an indication of whether the treatment event determined that the rhythm was shockable or non-shockable). In some examples, other data can also be stored. For instance, information from other victim monitoring devices, such as $SpO_2$ data, $CO_2$ data, ventilation data, chest compression data, and other data about the rescue attempt can be stored synchronously with the victim's ECG trace. In some examples, a narrative can be stored with the victim's ECG trace. For instance, the communications module 206 can record the caregiver's comments and the recorded comments can be stored synchronously with the victim's ECG trace.

The victim's ECG trace can provide information that can be used to aid in diagnosing and treating the victim. In particular, the victim's ECG trace prior to receiving a shock can provide information that can be used to diagnose the victim's condition. Knowledge of the victim's likely diagnosis can inform treatment of the victim, both at the rescue scene 100 and in a hospital setting.

The portion of the ECG trace associated with an initial treatment event (e.g., corresponding to an initial treatment period during which the AED 200 was first connected to the victim 102, such as within the first 6-10 seconds) can provide information about the victim's pathology. For instance, this initial portion of the ECG trace can help to identify the victim's pathology as pulseless electrical activity (PEA), ST-elevation myocardial infarction (STEMI), ventricular arrhythmia, atrial arrhythmia, preeclampsia, or another cardiac pathology. If the victim's pathology can be identified, appropriate treatment can be delivered to the victim.

The portion of the ECG trace associated with each analysis period (e.g., the portion of the ECG trace during the analysis period prior to delivery of a shock or determination that the rhythm is non-shockable) can provide information about the types of rhythms that developed in the victim. In some cases, a shockable rhythm that occurs once in a victim may not occur again after defibrillation. Storing the ECG traces prior to delivery of a shock can serve as a catalog of the types of rhythms that developed in the victim, even if those rhythms occur only once or a small number of times. Knowledge of the rhythms that developed in the victim can inform decisions about diagnosis and treatment of the victim.

The communications module 206 causes representations of the stored portions of the ECG trace to be transmitted, e.g., to the display interface 210 of the AED 200, such as a liquid crystal display (LCD) screen or another type of display interface; or to another computing device. For instance, the portions of the ECG traces can be transmitted to a computing device used by a caregiver at the rescue scene 100 or a medical professional at a hospital. The transmitted portions of the ECG trace can be displayed on the display interface 210 of the AED or on another computing device as still images or can be played back as videos.

In some examples, a representation of the portion of the ECG trace for one or more treatment events (e.g., the initial treatment period and/or one or more of the analysis periods) is automatically presented sequentially on the display interface 210. For instance, the representation of the portion of the ECG trace can be the portion of the ECG trace itself. In some examples, identifiers of multiple treatment events (e.g., identifiers indicative of the time of each treatment event) are displayed on the display interface 210, e.g., as a list, and the caregiver 102 can select to view the portions of the ECG trace for one or more of the listed treatment events. In some examples, identifiers of the types of rhythms exhibited by the victim 102 are displayed on the display interface 210, e.g., as a list, and the caregiver 102 can select to view all of the portions of the ECG trace associated with a particular type of rhythm, such as all shockable rhythms, all non-shockable rhythms, or a specific type of rhythm (e.g., ventricular fibrillation, asystole, or another specific type of rhythm).

The caregiver 104 can interact with the displayed portions of the ECG trace, e.g., to move forwards or backwards in time along a trace, to zoom in, to switch from the trace of one analysis period to the trace of another analysis period, etc. In some examples, the caregiver 104 can interact with the display interface 210 by clicking on the display interface 210 with a mouse or other pointing device, by typing commands into a keyboard or a keypad, or by using buttons provided on the AED 200. In some examples, the display interface 210 is a touch-responsive interface, and the caregiver 104 can interact with the display interface 210 by touching, tapping, or dragging on the display interface 210 with a finger or stylus. In some examples, the AED 200 includes voice recognition capabilities and the caregiver 104 can interact with the display interface 210 by speaking commands.

In some examples, the stored portions of the ECG trace can be displayed on the display interface 210 responsive to a user request. For instance, during or after treatment of the victim 102, a caregiver can request to view the stored portions of the ECG trace, e.g., to see the history of the victim's treatment.

Figure 1B:
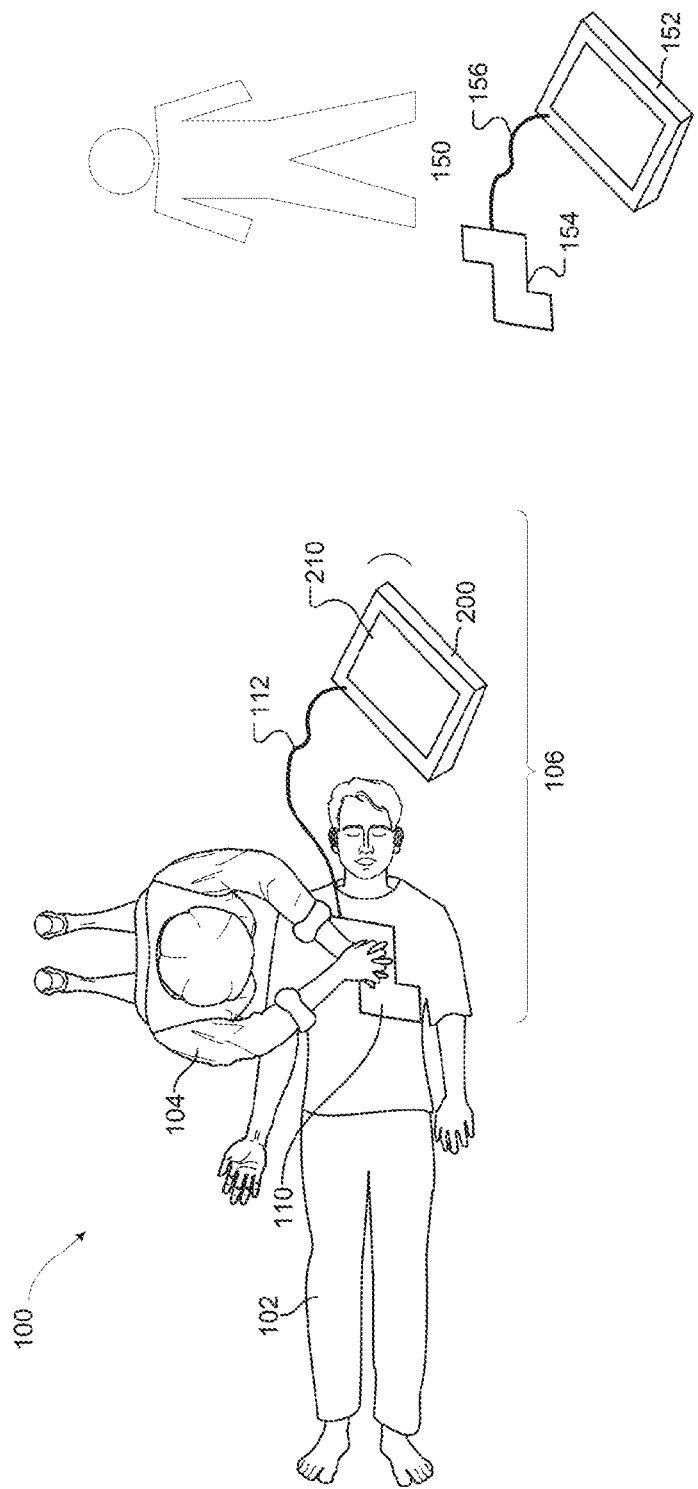

In some examples, the stored portions of the ECG trace can be displayed on the display interface 210 once the AED 200 has been disconnected from the victim 102. For instance, referring to FIG. 1B, if a highly trained second caregiver 150 (e.g., a paramedic, an EMT, an advanced life support team, or another trained caregiver), it can be beneficial for the second caregiver 150 to understand the history of the victim's 102 cardiac rhythms. This information can include the rhythms present at key times during the treatment, such as when treatment was first initiated and when the rhythms were identified as shockable or non-shockable. The rhythms during these periods can be displayed to the second caregiver 150.

Particularly, in some examples, the second caregiver 150 can arrive with a more advanced defibrillator 152. The caregiver 104 can stop treating the victim 102 with the AED 200 and allow the second caregiver 150 to take over treatment using the advanced defibrillator 152. The second caregiver 150 can remove the electrode pads 110 from the victim 102, thus disconnecting the AED 200 from the victim 102. The second caregiver can then position new electrode pads 154 on the victim 102 that are connected to the advanced defibrillator 152 via cables 156. In some cases, the electrode pads 110 are compatible with the advanced defibrillator 152, and the second caregiver 150 can disconnect the cables 112 from the AED 200 (thus disconnecting the AED 200 from the victim 102) and connect the cables 112 to the same advanced defibrillator 152.

Referring again to FIG. 2, a detection module 212 detects when the AED 200 is disconnected from the victim 102. For instance, the detection module 212 can detect when a significant change occurs in the impedance across the victim's chest between the two electrode pads 110 by detecting a loss of impedance in a circuit that includes the AED 200 and the victim 102. That is, when the electrode pads 110 are removed from the victim 102 or when the cables 112 are disconnected from the electrode pads 110, the detection module 212 detects a corresponding loss of impedance. Based on the loss of impedance, the detection module 212 determines that the AED 200 has been disconnected from the victim 102. For instance, the detection module 212 can detect when the loss of impedance is greater than a threshold change or when the actual impedance falls below a threshold value. The threshold change or threshold value can be set such that small changes in impedance, e.g., due to cardiac activity of the victim, the victim's respiration or ventilation, or other activities, do not register as a disconnection of the AED 200.

When the detection module 212 detects that the AED 200 has been disconnected, the communications module 206 can ask for confirmation that treatment with the AED has been completed. Once confirmation is received, the communications module 206 causes the stored portions of the victim's ECG trace to be transmitted. In one example, a confirmation message is displayed on the display interface 210 asking a caregiver (e.g., caregiver 104 or 150) to confirm that treatment with the AED 200 has ended. In one example, an audio confirmation message can be played through a speaker in the AED 200 and a caregiver can respond verbally. The caregiver's verbal response can be processed by voice recognition software implemented in the communications module 206.

In some examples, the communications module 206 can ask for confirmation as soon as the detection module 212 detects a loss of impedance. In some examples, the communications module 206 can ask for confirmation after a waiting period, such as 2 seconds, 5 seconds, or 10 seconds after the detection module 212 detects a loss of impedance. The waiting period can help avoid asking the caregiver for confirmation in response to an accidental disconnection of the AED 200 (e.g., by accidentally dislodging a cable 112).

The ability to view portions of the victim's ECG trace at the rescue scene can provide critical, lifesaving information to the caregivers at the rescue scene 100. For instance, the initial caregiver 104 may be a relatively untrained caregiver who does not know how to read ECG traces. That is, the caregiver 104 may be unable to communicate information about the victim's initial ECG trace and information about the portions of the ECG trace in the analysis periods to the highly trained caregiver 150. By providing the caregiver 150 with the ability to view portions of the victim's ECG trace, the caregiver 150 has rapid access to information that can enable him to make more informed decisions about treatment options for the victim 102 (e.g., information about the victim's condition when he first collapsed or information about the rhythms that triggered shock events). For instance, the caregiver 150 can use this information to decide which medications to administer, whether to continue with CPR or defibrillation treatment, how urgently to bring the victim to an emergency room, and other decisions. In addition, the caregiver 150 can communicate this information to other medical personnel, such as emergency room nurses or physicians, without having to download the ECG traces or transport the AED 200 itself to the emergency room.

In some examples, the communications module 206 provides the ability to download portions of the victim's ECG trace and other monitoring data to a computing device, such as a mobile computing device (e.g., a laptop computer, a mobile phone, a tablet, a watch, glasses, or another type of mobile computing device) or to a storage device, such as a USB drive. For instance, the computing device or storage device can be connected to a data port on the AED 200, e.g., directly or via a cable connection. In some examples, the portions of the victim's ECG trace can be downloaded through a wireless connection between the AED 200 and the computing device, e.g., through a short-range wireless protocol such as Bluetooth® communication or another type of wireless communication. For instance, the victim's traces and other monitoring data can be downloaded to a computer at a hospital to allow a physician to view details of the victim's treatment history.

Figure 3:
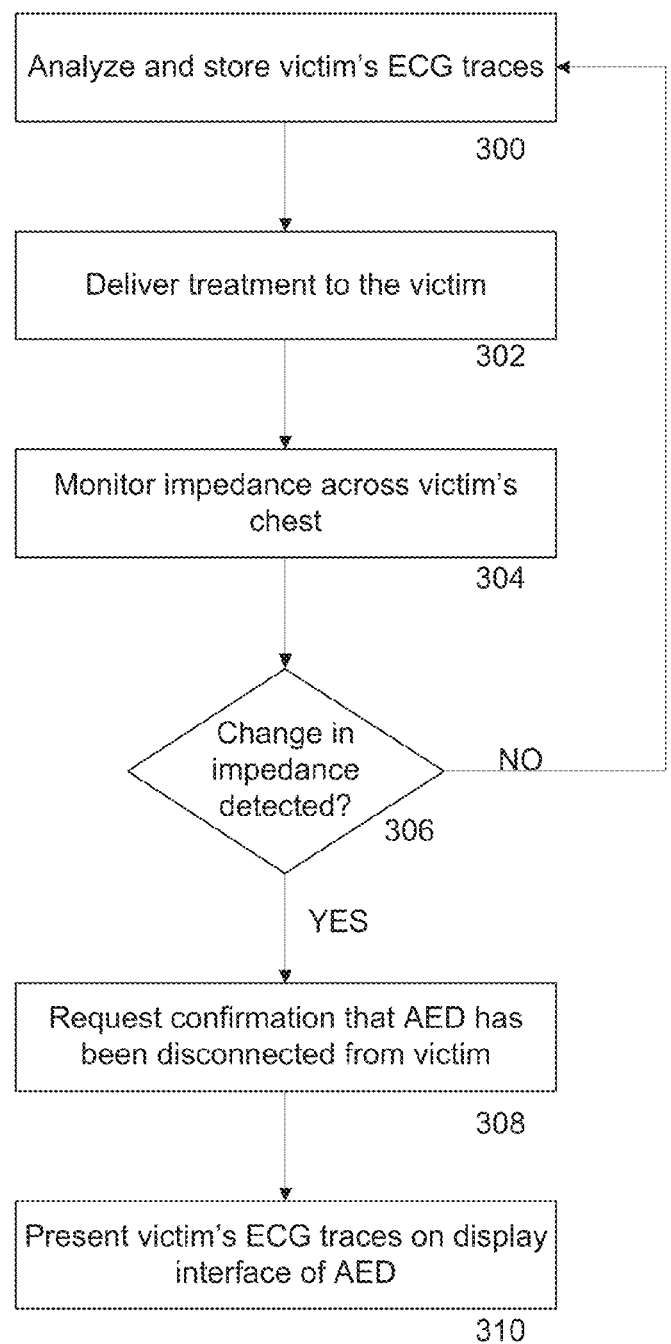
FIG. 3 is a flowchart.

Referring to FIG. 3, in one example of an approach to providing care to a victim, an AED analyzes, identifies, and stores portions of a victim's ECG trace during treatment of the victim with the AED, e.g., while the AED is connected to the victim (300). Other monitoring data, and other monitoring information, such as $SpO_2$ data, $CO_2$ data, ventilation data, chest compression data, and other data about the rescue attempt, can also be stored synchronously with the portions of the victim's ECG trace. For instance, the AED analyzes the victim's rhythms periodically, e.g., once per minute, once every 2 minutes, once every 3 minutes, or another time period. The analysis period can be, e.g., 9 seconds, 12 seconds, 15 seconds, or another analysis period. The analysis of the victim's rhythms includes identify the type of rhythm and determining whether the rhythm is shockable or non-shockable. The portions of the ECG trace for at least each analysis period are stored on the AED.

Treatment is delivered to the victim (302). For instance, if the victim's rhythm is shockable, the AED can deliver a shock to the victim. The AED can instruct a caregiver to deliver chest compressions to the victim, e.g., following delivery of a shock or if the victim's rhythm is non-shockable.

During the treatment of the victim, the impedance across the victim's chest is monitored (304). For instance, the impedance across the victim's chest can be monitored continuously or periodically, e.g., once per second, once every 2 seconds, once every 5 seconds, or another time period. If no significant change in impedance is detected (306), the analysis and storage of the victim's rhythms (300) and the delivery of treatment (302) continue.

When a significant change in impedance is detected (306), the AED asks for confirmation that the AED has been disconnected from the victim (308). In some examples, the AED asks for confirmation after a waiting period of, e.g., 10 seconds after detecting a significant change in the impedance. The significant change in impedance can include that the change in impedance is greater than a threshold change in impedance or that the absolute value of the impedance is less than a threshold value. This significant change in impedance can indicate that the AED has been disconnected from the victim, e.g., by removing the electrode pads from the victim's chest or by disconnecting the electrode cables from the AED.

Upon receiving confirmation that the AED has been disconnected from the victim, the portions of the victim's ECG trace are presented on a display interface of the AED (310). In some examples, the portion of the ECG trace for each analysis period is automatically presented sequentially. In some examples, identifiers of treatment events associated with one or more of the analysis periods are displayed and a caregiver can select to view the portion of the ECG trace associated with one or more of the listed treatment events. In some examples, identifiers of one or more of the types of rhythms exhibited by the victim are displayed and a caregiver can select to view all of the portions of the ECG trace associated with a particular type of rhythm.

In some examples, some of the functionality of the AED 200 is carried out on a control device, such as a mobile device (e.g., a mobile phone, tablet, watch, glasses, or another type of mobile device). For instance, one or more of the analysis module 202, the communications module 206, the storage module 208, the display interface 210, and the detection module 212 can be implemented on the control device. An example control device is described in U.S. application Ser. No. 14/036,503, filed Sep. 25, 2013, the contents of which are incorporated herein by reference.

In some examples, a user of a mobile device can request to review the portions of the victim's ECG trace even if the AED has not been disconnected from the victim. For instance, while treatment is ongoing, a user can view the portions of the victim's ECG trace from earlier in treatment to gain an overview of how the victim's condition has progressed.

Figure 4:
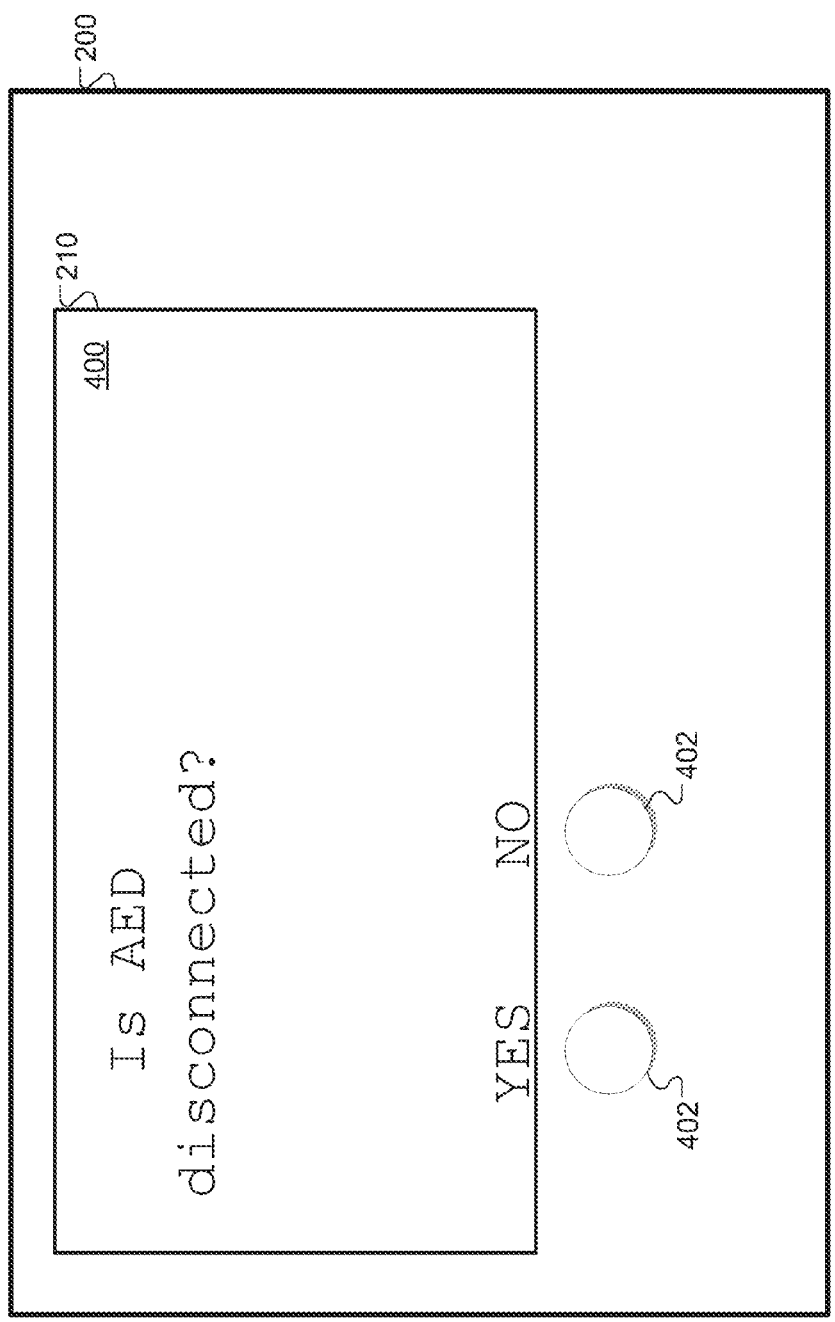
FIGS. 4-9 are screenshots.

Referring to FIG. 4, in one example, when a significant loss of impedance or other triggering event is detected, a confirmation screen 400 is displayed on the display interface 210 of the AED 200. The confirmation screen 400 asks a caregiver to confirm that the AED 200 has been disconnected from the victim. The caregiver can respond by touching or tapping on the display interface 210 or by pushing a button 402.

Figure 5:
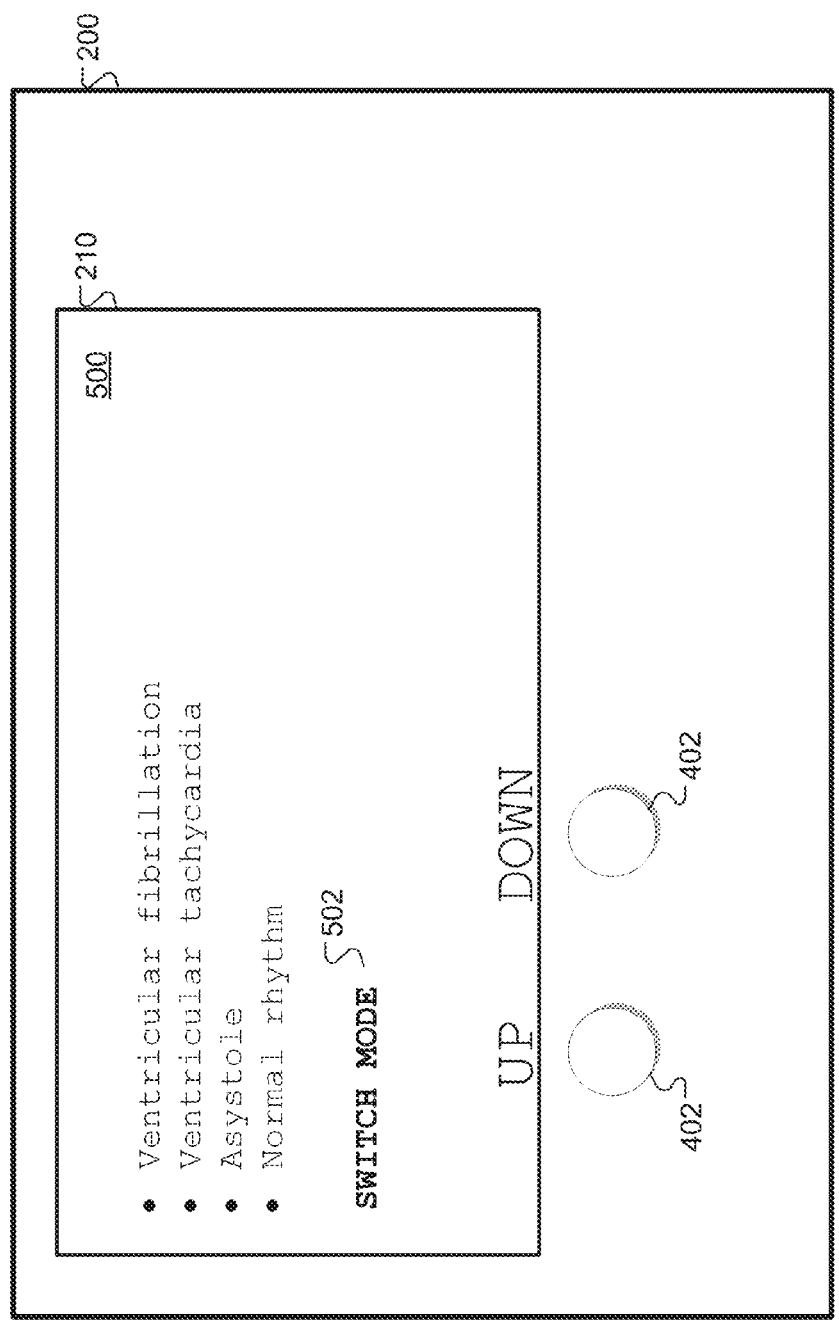

Referring to FIG. 5, in this example, after confirmation is received, a rhythms screen 500 displays a list of identifiers of all of the types of rhythms that occurred during treatment of the victim. The caregiver can select a type of rhythm to view the portions of the ECG traces in which the selected type of rhythm occurred by touching or tapping on the display interface or by pushing a button, if available. The caregiver can scroll up or down through the list of rhythms using the buttons 402. To view a chronological list of events (e.g., the timeline screen 800, described below) or a graphical timeline (e.g., the graphs screen 900, described below), the caregiver can select a "Switch Mode" option 502. In some examples, the types of rhythms that occurred during treatment of the victim are categorized as either "shockable" or "not shockable" on the rhythms screen 500.

Figure 6:
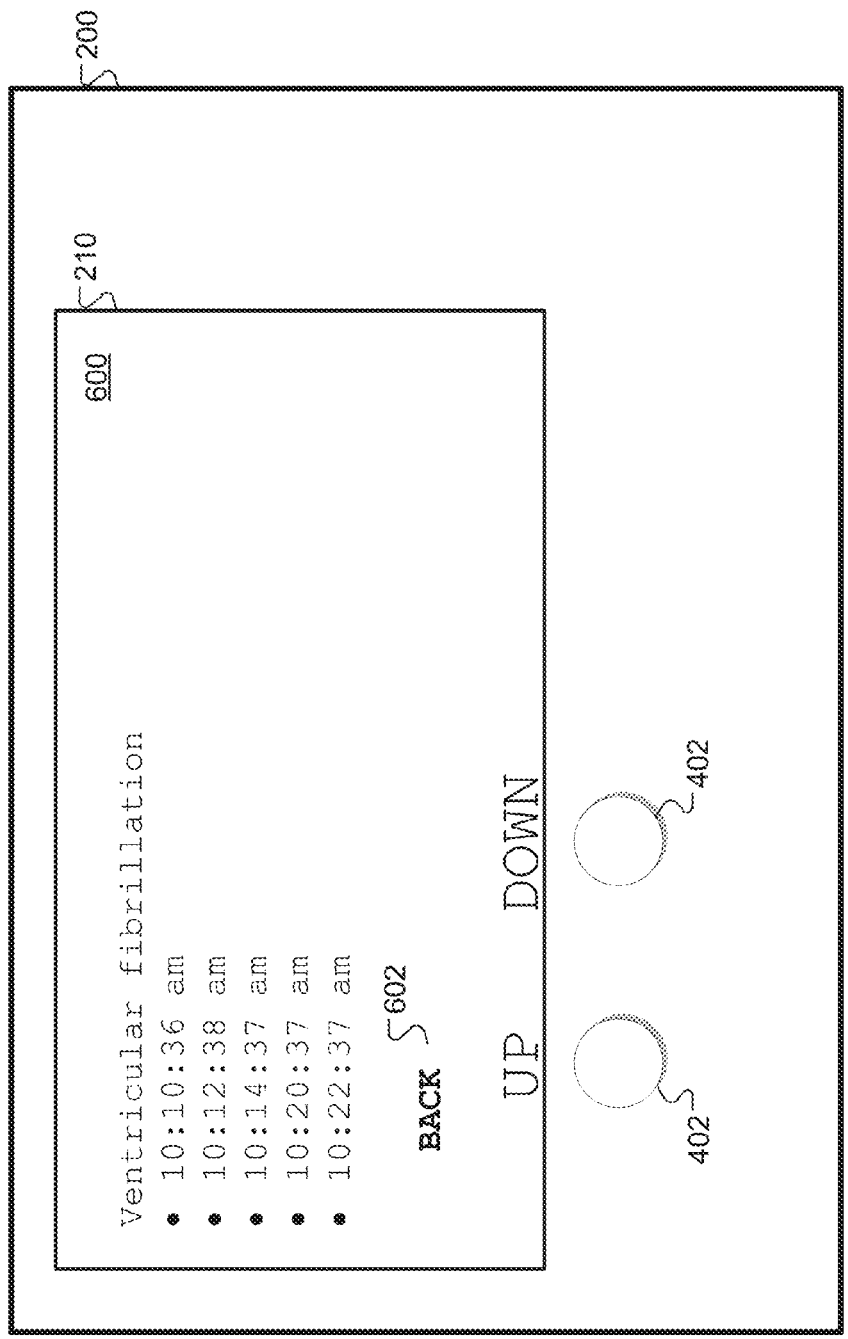

Referring to FIG. 6, in this example, the caregiver selected to view the portions of the ECG trace in which ventricular fibrillation was identified. An events screen 600 displays a list of all of the occurrences of ventricular fibrillation (e.g., all of the analysis periods in which ventricular fibrillation occurred). The occurrences can be identified by the number of the corresponding treatment event, by the timestamp of the corresponding treatment event, or by another identifier. In the example of FIG. 6, two periods of ventricular fibrillation occurred: one spanning three analysis periods between 10:10 and 10:14, and the second spanning two analysis periods between 10:20 and 10:22. The caregiver can select one of the treatment events to view the portion of the ECG trace associated with that treatment event (e.g., the portion of the ECG trace for the analysis period preceding the selected treatment event) by touching or tapping on the display interface. The caregiver can scroll up or down through the list of occurrences using the buttons 402. The caregiver can return to the rhythms screen 500 by selecting a "Back" option 602.

Figure 7:
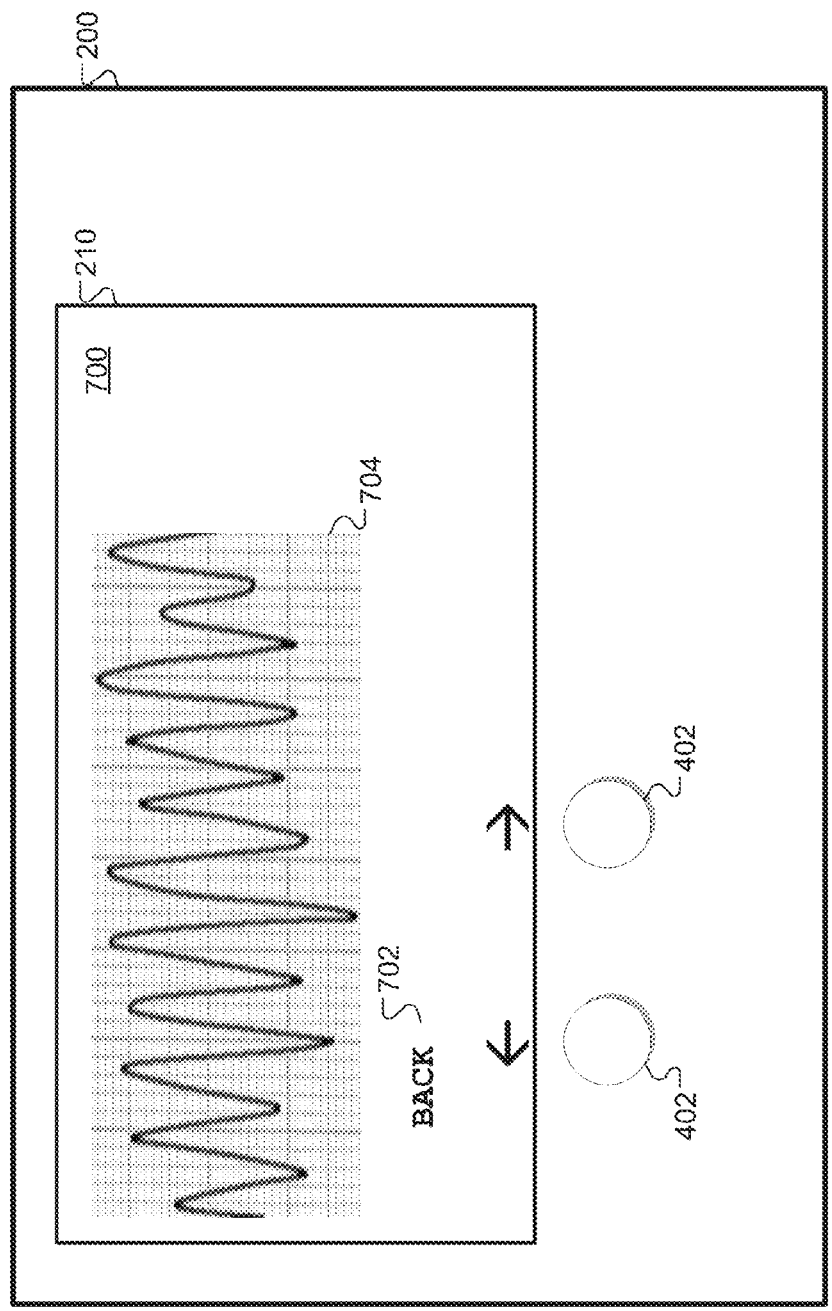

Referring to FIG. 7, in this example, the caregiver selected to view the first occurrence of ventricular fibrillation. A trace screen 700 displays a portion 704 of an ECG trace corresponding to this occurrence. In some examples, the caregiver can interact with the portion 704 of the ECG trace, e.g., by zooming in or out or scrolling forwards or backwards in time. From the trace screen 700, the caregiver can scroll to the trace for the previous analysis period or the next analysis period, e.g., by swiping to the right or left on the screen or by using the buttons 402. The caregiver can return to the previous screen by selecting a "Back" option 702.

Figure 8:
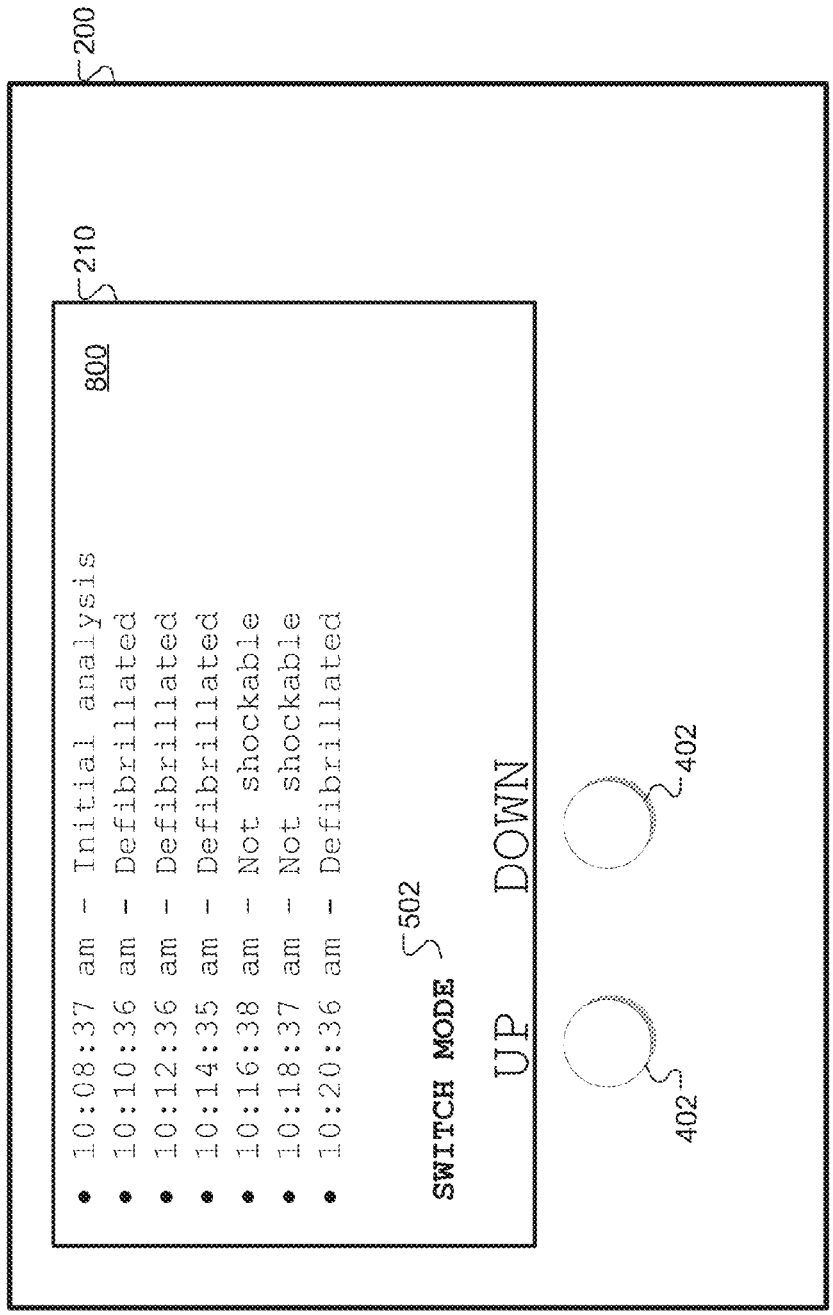

Referring to FIG. 8, in another viewing mode, a chronological list of treatment events can be displayed on a timeline screen 800. The timeline screen 800 displays a menu of identifiers of the treatment events in chronological order. The treatment events can be identified by number, by timestamp, or by another identifier. In some examples, the action taken at each treatment event (e.g., shock or no shock), the type of rhythm identified in the analysis period preceding each treatment event, or both can also be displayed. Selecting one of the treatment events brings up a display of the portion of the ECG trace associated with the selected treatment event, such as the portion of the ECG trace for the analysis period preceding the selected treatment event (e.g., such as trace screen 700). The caregiver can scroll up or down through the list of treatment events using the buttons 402. To view a list of the types of rhythms (e.g., the rhythms screen 500) or a graphical timeline (e.g., the graphs screen 900), the caregiver can select the "Switch Mode" option 502.

Figure 9:
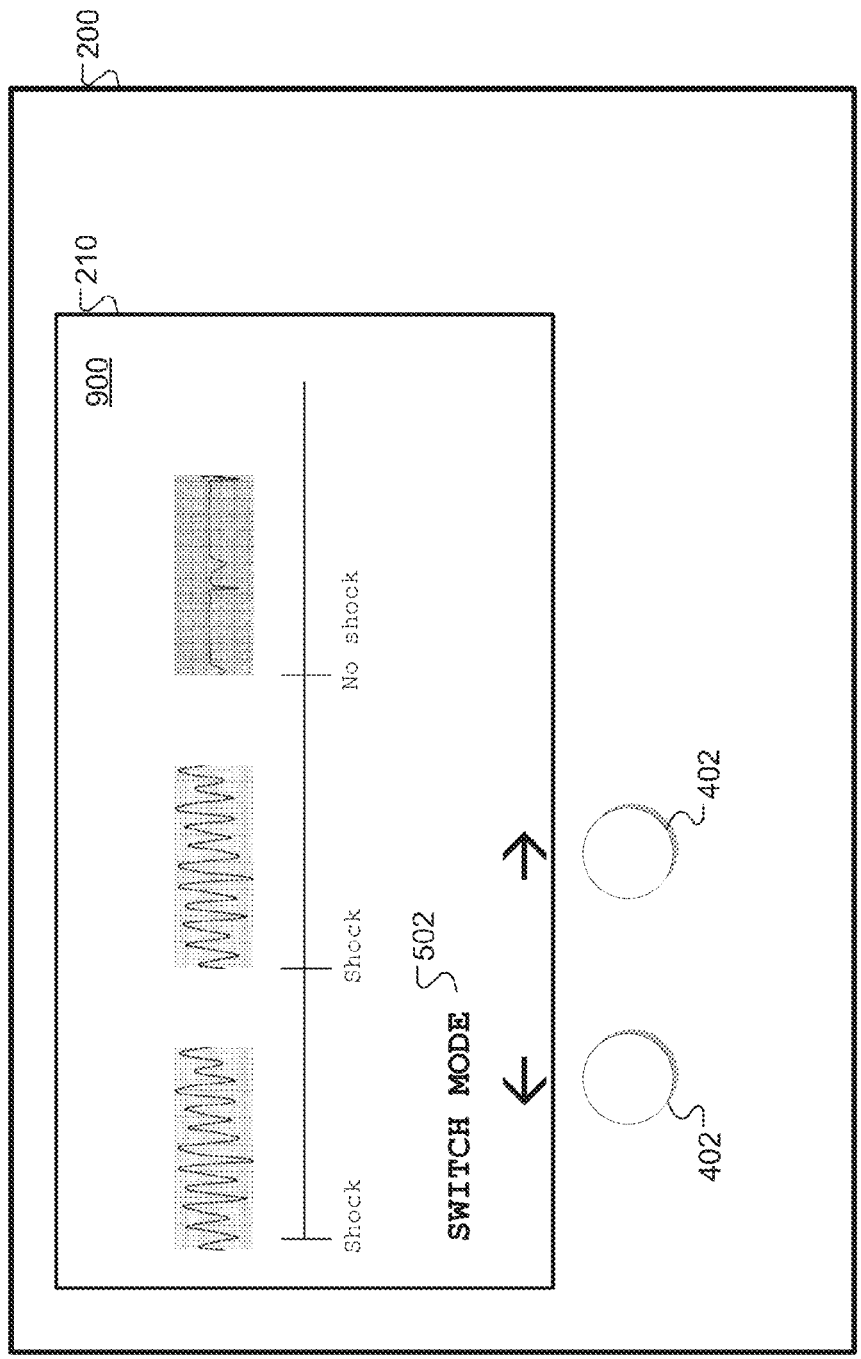

Referring to FIG. 9, in another viewing mode, a graphical timeline view of treatment events can be displayed on a graph screen 900. The graph screen displays a horizontal timeline of the treatment events in chronological order with a brief description of each treatment event. Selecting one of the treatment events brings up a display of the portion of the ECG trace associated with the selected treatment event, such as the portion of the ECG trace for the analysis period preceding the selected treatment event (e.g., such as trace screen 700). The caregiver can scroll forwards or backwards through the horizontal timeline using the buttons 402. To view a list of the types of rhythms (e.g., the rhythms screen 500), a textual timeline (e.g., the timeline screen 800), the caregiver can select the "Switch Mode" option 502.

The features described herein can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented on a mobile computing device, such as a mobile phone, a tablet, a watch, glasses, or another type of mobile computing device. The mobile computing device can have a display device such as a touch screen for displaying information to the user and receiving input from the user. The mobile computing device can receive input from the user via the touch screen, a key pad, a microphone, or another type of input device.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

It is to be understood that the foregoing description is intended to illustrate and not to limit the scope of the invention, which is defined by the scope of the appended claims. Other embodiments are within the scope of the following claims.

What is claimed is:

1. A defibrillating system comprising:
    a processor coupled to a memory, the processor and the memory configured to:
        determine that treatment of a patient using the defibrillating system is completed; and
        upon determining that treatment of the patient using the defibrillating system is complete, provide, for a user, a representation of a portion of a physiological signal obtained by the defibrillating system during treatment of the patient.

2. The defibrillating system of claim 1, wherein determining that treatment of the patient is completed comprises detecting that the defibrillating system has been disconnected from the patient.

3. The defibrillating system of claim 2, wherein detecting that the defibrillating system has been disconnected from the patient comprises detecting a change in impedance in a circuit that includes the defibrillating system and the patient.

4. The defibrillating system of claim 1, wherein the physiological signal comprises an electrocardiogram (ECG) signal.

5. The defibrillating system of claim 4, wherein the processor and memory are further configured to identify a portion of the ECG signal analyzed by the defibrillating system in determining whether to deliver treatment to the patient; and
    wherein providing a representation of a portion of a physiological signal comprises providing the identified portion of the ECG signal.

6. The defibrillating system of claim 4, wherein the processor and memory are further configured to provide an identifier associated with the portion of the ECG signal.

7. The defibrillating system of claim 6, wherein the identifier associated with the portion of the ECG signal comprises a time associated with the portion of the ECG signal.

8. The defibrillating system of claim 6, wherein the identifier associated with the portion of the ECG signal comprises an indication of whether the portion of the ECG signal represents a shockable cardiac rhythm or a non-shockable cardiac rhythm.

9. The defibrillating system of claim 6, wherein the identifier associated with the portion of the ECG signal comprises an identifier of a type of cardiac rhythm represented by the identified portion of the ECG signal.

10. The defibrillating system of claim 1, wherein the physiological signal comprises one or more of an $SpO_2$ signal, a $CO_2$ signal, a ventilation signal, and a chest compression signal.

11. The defibrillating system of claim 1, wherein the processor and memory are further configured to provide audio information associated with the portion of the physiological signal.

12. The defibrillating system of claim 1, wherein providing a representation of the portion of the physiological signal comprises displaying the representation of the portion of the physiological signal on a display interface of the defibrillating system.

13. The defibrillating system of claim 1, wherein providing a representation of the portion of the physiological signal comprises transmitting the representation of the portion of the physiological signal to a computing device.

14. The defibrillating system of claim 1, wherein the computing device comprises a wearable computing device.

15. A computer readable medium storing instructions for causing a defibrillating system to:
   determine that treatment of a patient using the defibrillating system is completed; and
   upon determining that treatment of the patient using the defibrillating system is complete, provide, for a user, a representation of a portion of a physiological signal obtained by the defibrillating system during treatment of the patient.

16. The computer readable medium of claim 15, wherein determining that treatment of the patient is completed comprises detecting that the defibrillating system has been disconnected from the patient.

17. The computer readable medium of claim 15, wherein the physiological signal comprises an electrocardiogram (ECG) signal.

18. The computer readable medium of claim 17, storing instructions for causing the defibrillating system to identify a portion of the ECG signal analyzed by the defibrillating system in determining whether to deliver treatment to the patient; and
   wherein providing a representation of a portion of a physiological signal comprises transmitting the identified portion of the ECG signal.

19. The computer readable medium of claim 17, wherein the processor and memory are further configured to provide an identifier associated with the portion of the ECG signal.

20. The computer readable medium of claim 15, wherein the physiological signal comprises one or more of an $SpO_2$ signal, a $CO_2$ signal, a ventilation signal, and a chest compression signal.

21. The computer readable medium of claim 15, storing instructions for causing the defibrillating system to provide audio information associated with the portion of the physiological signal.

22. The computer readable medium of claim 15, wherein providing a representation of the portion of the physiological signal comprises displaying the representation of the portion of the physiological signal on a display interface of the defibrillating system.

23. The computer readable medium of claim 15, wherein providing a representation of the portion of the physiological signal comprises transmitting the representation of the portion of the physiological signal to a computing device.

* * * * *